US00PP29076P3

(12) United States Plant Patent
Beekenkamp

(10) Patent No.: US PP29,076 P3
(45) Date of Patent: Mar. 6, 2018

(54) ***LAVANDULA* PLANT NAMED 'BKLVSTFPU'**

(50) Latin Name: *Lavandula stoechas*
Varietal Denomination: BKLVSTFPU

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 4 days.

(21) Appl. No.: 14/999,999

(22) Filed: Jul. 25, 2016

(65) Prior Publication Data

US 2018/0027721 P1 Jan. 25, 2018

(51) Int. Cl.
*A01H 5/02* (2006.01)
*G11B 5/60* (2006.01)

(52) U.S. Cl.
USPC ..... Plt./445
CPC ..... *G11B 5/6005* (2013.01)

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'BKLVSTFPU', characterized by its compact and broadly upright plant habit; freely branching growth habit; early and freely flowering habit; purple-colored flowers with violet-colored bracts arranged on terminal spikes; and good garden performance.

2 Drawing Sheets

Botanical designation: *Lavandula stoechas.*
Cultivar denomination: 'BKLVSTFPU'.

BACKGROUND OF THE INVENTION

The present invention relates to a new and distinct *Lavandula* plant, botanically known as *Lavandula stoechas*, commonly referred to as Lavender and hereinafter referred to by the name 'BKLVSTFPU'.

The new *Lavandula* plant is a product of a planned breeding program conducted by the Inventor in Maasdijk, The Netherlands. The objective of the breeding program was to develop new compact and early-flowering *Lavandula* plants with good performance and attractive plant form and flower coloration.

The new *Lavandula* plant originated from an open-pollination in July, 2012 of a proprietary selection of *Lavandula stoechas* identified as code number 4300112, not patented, as the female, or seed, parent with an unknown selection of *Lavandula stoechas* as the male, or pollen, parent. The new *Lavandula* plant was discovered and selected by the Inventor as a single flowering plant within the progeny of the stated open-pollination in an outdoor nursery in Maasdijk, The Netherlands in July, 2013.

Asexual reproduction of the new *Lavandula* plant by terminal cuttings in a controlled outdoor nursery environment in Maasdijk, The Netherlands since September, 2013 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'BKLVSTFPU' as a new and distinct *Lavandula* plant:

1. Compact and broadly upright plant habit.
2. Freely branching growth habit.
3. Early and freely flowering habit.
4. Purple-colored flowers with violet-colored bracts arranged on terminal spikes.
5. Good garden performance.

Plants of the new *Lavandula* differ primarily from plants of the female parent selection in the following characteristics:

1. Plants of the new *Lavandula* are more compact than plants of the female parent selection.
2. Plants of the new *Lavandula* have broader inflorescences than plants of the female parent selection.
3. Plants of the new *Lavandula* and the female parent selection differ in flower color as plants of the female parent selection have dark pink-colored flowers.

Plants of the new *Lavandula* can be compared to plants of the *Lavandula stoechas* 'Bee Happy', disclosed in U.S. Plant Pat. No. 12,573. In side-by-side comparisons, plants of the new *Lavandula* differ primarily from plants of 'Bee Happy' in the following characteristics:

1. Plants of the new *Lavandula* are more compact and shorter than plants of 'Bee Happy'.
2. Plants of the new *Lavandula* and 'Bee Happy' differ in flower color as plants of 'Bee Happy' have purple-colored flowers with white-colored bracts.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'BKLVSTFPU' grown in a container.

The photograph on the second sheet is a close-up view of lower and upper surfaces of typical leaves, a typical flower bud and a typical flowering stem of 'BKLVSTFPU'.

DETAILED BOTANICAL DESCRIPTION

Plants used in the aforementioned photographs and following detailed description were grown in 12-cm containers during the spring and early summer in a glass-covered greenhouse in Maasdijk, The Netherlands and under cultural practices typical of commercial *Lavandula* production. Plants were pinched one time and were 23 weeks old when the photographs and description were taken. During the production of the plants, day temperatures ranged from 15° C. to 22° C. and night temperatures ranged from 12° C. to 16° C. In the following description, color references are made to The Royal Horticultural Society Colour Chart, 2015 Edition, except where general terms of ordinary dictionary significance are used.

Botanical classification: *Lavandula stoechas* 'BKLVSTFPU'.

Parentage:

*Female, or seed, parent*.—Proprietary selection of *Lavandula stoechas* identified as code number 4300112, not patented.

*Male, or pollen, parent*.—Unknown selection of *Lavandula stoechas*, not patented.

Propagation:

*Type*.—Terminal vegetative cuttings.

*Time to initiate roots, summer*.—About 28 days at temperatures ranging from 17° C. to 19° C.

*Time to initiate roots, winter*.—About 30 days at temperatures ranging from 18° C. to 19° C.

*Time to produce a rooted young plant, summer*.—About 48 days at temperatures ranging from 17° C. to 19° C.

*Time to produce a rooted young plant, winter*.—About 50 to 54 days at temperatures ranging from 17° C. to 19° C.

*Root description*.—Fine, fibrous; typically white in color, actual color of the roots is dependent on substrate composition, water quality, fertilizer type and formulation.

*Rooting habit*.—Moderately freely branching; medium density.

Plant description:

*Plant and growth habit*.—Herbaceous perennial; compact and broadly upright plant habit; roughly globular to broadly ovate in overall shape; moderately vigorous growth habit; moderate growth rate; flowers arranged in verticillasters on terminal spikes.

*Plant height, soil level to top of foliar plane*.—About 16.3 cm.

*Plant height, soil level to top of floral plane*.—About 22.6 cm.

*Plant width*.—About 21.3 cm.

*Lateral branch description*.—Quantity per plant: About nine primary lateral branches each with about ten secondary branches developing per plant during the flowering season. Length: About 6.5 cm. Diameter: About 1.5 mm. Internode length: About 2.9 cm. Strength: Moderately strong. Aspect: Upright to somewhat outwardly. Texture and luster: Densely tomentose; slightly glossy. Color, developing: Close to 144B to 144C; at the internodes, between 143C and 144B. Color, developed: Close to 199B and 199C.

*Leaf description*.—Arrangement: Opposite, simple; sessile. Length: About 3.2 cm. Width: About 5 mm. Shape: Narrowly oblanceolate. Apex: Acute. Base: Cuneate. Margin: Entire; slightly to moderately revolute. Texture and luster, upper surface: Densely pubescent; matte. Texture and luster, lower surface: Moderately to densely pubescent; matte. Fragrance: Strongly aromatic, pungent. Venation pattern: Pinnate. Color: Developing leaves, upper surface: Close to 137B. Developing leaves, lower surface: Close to 138B. Fully expanded leaves, upper surface: Close to NN137B to NN137C; venation, close to 138A. Fully expanded leaves, lower surface: Close to 137B; venation, close to 138B.

Flower description:

*Flower type, arrangement and habit*.—Small single salverform flowers arranged in verticillasters on terminal spikes; freely flowering habit with about 115 flowers developing per inflorescence and about 3,850 flowers developing per plant; flowers with two-lobed upper lip and three-lobed lower lip; flowers face mostly outwardly on the spike.

*Natural flowering season*.—Relatively long flowering period; continuous from late spring into the summer in The Netherlands.

*Flower longevity on the plant*.—Individual flowers last about 50 days on the plant; flowers not persistent.

*Fragrance*.—None detected.

*Flower buds*.—Length: About 7 mm. Diameter: About 2 mm. Shape: Elliptic. Texture and luster: Moderately tomentose; matte. Color: Close to 143B; distally, tinged with close to N186C; at the apex, close to N186A.

*Inflorescence height*.—About 4.9 cm.

*Inflorescence diameter*.—About 1.8 cm.

*Flower diameter*.—About 7 mm.

*Flower depth (height)*.—About 1.1 cm.

*Petals*.—Quantity and arrangement: Upper lip, two-lobed and lower lip, three-lobed. Length, upper lip: About 1 cm. Length, lower lip: About 9 mm. Width, upper lip: About 2 mm. Width, lower lip: About 2 mm. Shape: Roughly spatulate; lower 70% fused into a tube. Apex: Obtuse, rounded. Margin: Entire. Texture and luster, upper (inner) surface: Smooth, glabrous; slightly velvety; matte. Texture and luster, lower (outer) surface: Smooth, glabrous; slightly velvety; slightly glossy. Color: When opening, upper (inner) and lower (outer) surfaces: Close to N186A. Fully opened, upper (inner) surface: Close to between N92A and N186B; throat, close to 86A to 86B; color becoming closer to N186A with development. Fully opened, lower (outer) surface: Close to between N92A and N186B; tube, close to 86C and proximally, close to N87D; color becoming closer to N186A with development.

*Basal flower bracts*.—Quantity and arrangement: Each group of seven flowers is subtended by a single basal flower bract. Length: About 1 cm. Width: About 9 mm. Shape: Broadly rhomboidal. Apex: Broadly aristate. Base: Cuneate. Margin: Entire. Texture and luster, upper and lower surfaces: Sparsely tomentose; matte. Color, upper surface: Close to 187C; venation, close to 146B. Color, lower surface: Close to 187C; venation, close to between N186B and N200A.

*Sterile flower bracts*.—Quantity and arrangement: Four sterile flower bracts at apex of spike. Length: About 2.2 cm. Width: About 9 mm. Shape: Narrowly elliptic to narrowly oblong to narrowly obovate. Apex: Acute. Base: Cuneate. Margin: Entire; undulate. Texture and luster, upper and lower surfaces: Sparsely tomentose; matte. Color, upper surface: Close to N82B; main vein, tinged with close to N186B. Color, lower surface: Close to N82B; main vein, close to 187A.

*Sepals*.—Quantity and arrangement: Five, fused into a campanulate tube. Calyx length: About 7 mm. Calyx diameter: About 2 mm. Shape: Lanceolate. Apex: Acute. Margin: Entire. Texture and luster, upper (inner) and lower (outer) surfaces: Densely pubescent; moderately glossy to glossy. Color: When opening, upper (inner) surface: Close to 145A; venation, close to 143A. When opening, lower (outer) surface: Close to 143B; distally, tinged with close to N186C. Fully opened, upper (inner) surface: Close to 145A; venation, close to 143A. Fully opened, lower (outer) surface: Close to 143A.

*Peduncles*.—Length: About 5.3 cm. Diameter: About 2 mm. Aspect: Mostly upright. Strength: Strong. Texture and luster: Densely tomentose; matte. Color: Close to 144A; distally, tinged with close to 176A.

*Reproductive organs*.—Stamens: Quantity per flower: Four. Filament length: About 1 mm. Filament color: Close to 84D. Anther shape: Reniform. Anther length: About 0.75 mm. Anther color: Close to 21B to 21C. Pollen amount: Scarce to moderate. Pollen color: Close to 14A to 14B. Pistils: Quantity per flower: One. Pistil length: About 4 mm. Stigma diameter: About 0.5 mm. Stigma shape: Club-shaped. Stigma color: Close to N186A. Style length: About 3.5 mm. Style color: Close to 85C. Ovary color: Close to 143A to 143B.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and to be suitable for USDA Hardiness Zones 8 to 10.

It is claimed:

1. A new and distinct *Lavandula* plant named 'BKLVST-FPU' as illustrated and described.

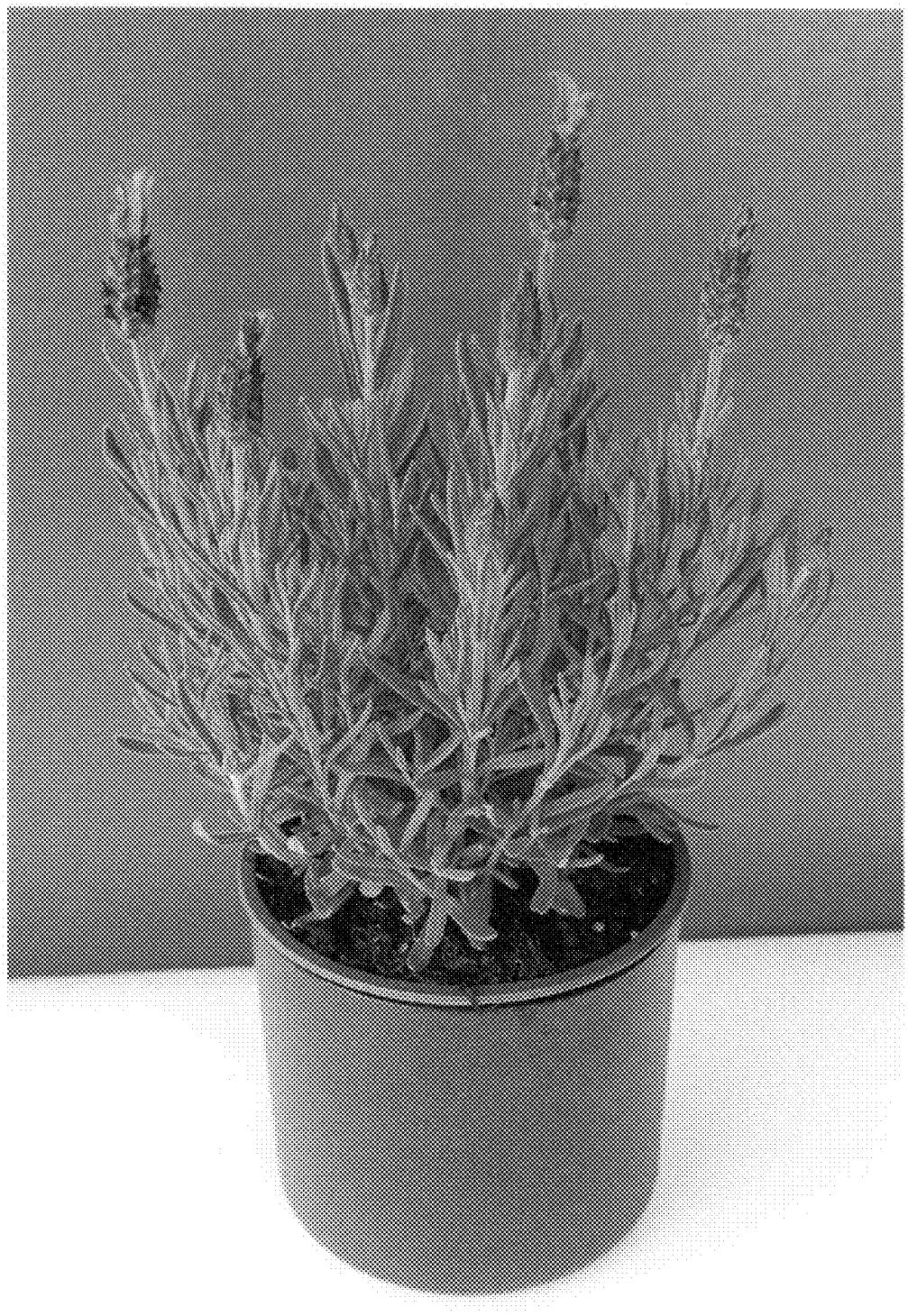

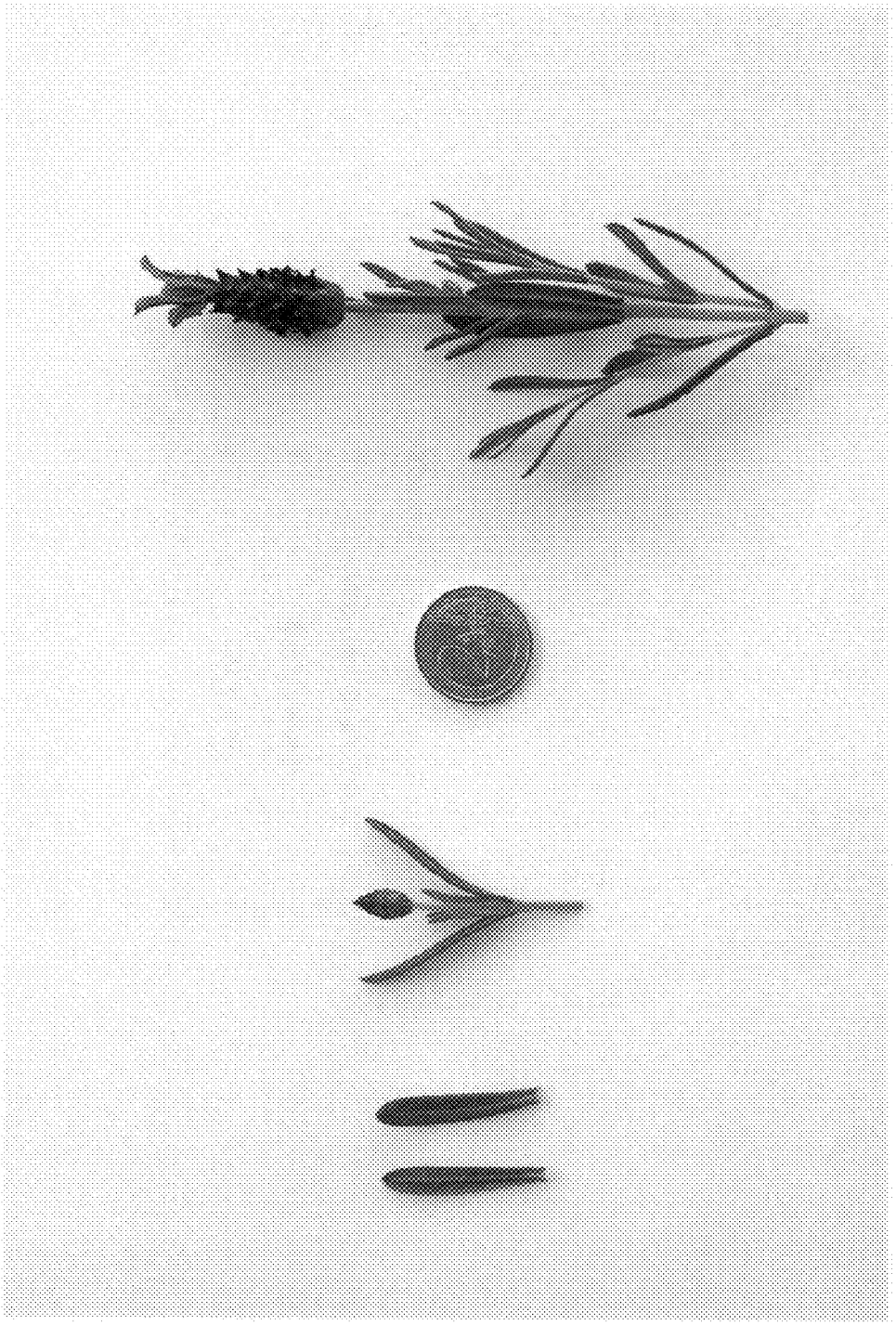

* * * * *